United States Patent [19]

Ottimo

[11] Patent Number: 4,915,219
[45] Date of Patent: Apr. 10, 1990

[54] DISINFECTING TOOTHBRUSH CONTAINER

[76] Inventor: Anthony Ottimo, 75 Kristin La., Hauppauge, N.Y. 11788

[21] Appl. No.: 261,493

[22] Filed: Oct. 24, 1988

[51] Int. Cl.[4] .............................................. B65D 81/00
[52] U.S. Cl. .............................. 206/209.1; 206/362.1; 422/28
[58] Field of Search ..................... 206/209, 209.1, 362, 206/362.1, 362.3; 220/20; 422/28

[56]         References Cited
U.S. PATENT DOCUMENTS

| | | | |
|---|---|---|---|
| 741,321 | 10/1903 | Flower | 206/362.3 |
| 757,885 | 4/1904 | Cochrane | 206/209 |
| 827,308 | 7/1906 | Hitch | 206/209.1 |
| 880,432 | 2/1908 | Weidhaas, Jr. | 206/209.1 |
| 1,070,858 | 8/1913 | Trayne | 206/209.1 X |
| 1,465,627 | 8/1923 | Fisher et al. | 206/362.1 X |
| 1,586,332 | 5/1926 | Scott | 206/209.1 |
| 1,611,304 | 12/1926 | Coston | 206/362.1 |
| 3,574,879 | 4/1971 | Werding | 206/362.2 |
| 3,741,378 | 6/1973 | Parker | 206/209 |
| 3,881,868 | 5/1975 | Duke | 206/209.1 |
| 3,904,362 | 9/1975 | DiPaolo | 206/209 X |
| 4,214,657 | 7/1980 | Winston | 206/209.1 |
| 4,473,152 | 9/1984 | Jump, Jr. et al. | 206/209 |
| 4,585,119 | 4/1986 | Boyington | 206/209 X |

FOREIGN PATENT DOCUMENTS 972717  8/1950  France .................................. 206/209

*Primary Examiner*—William Price
*Attorney, Agent, or Firm*—Rosen, Dainow & Jacobs

[57]                ABSTRACT

The disinfecting toothbrush container for holding the toothbrush and disinfecting the bristles of the toothbrush comprises a container body having a plurality of container chambers formed by dividing the container body by a plurality of substantially vertical container chamber walls. The container chambers are divided transversely by a substantially transverse flexible rubber partition having a slit in each of the container chambers large enough for insertion of the toothbrush. The transverse flexible partition divides each container chamber into an upper portion containing air and a lower portion containing a disinfecting liquid. The lips of each of the slits are firm enough to prevent dirt and germs from the air from entering the disinfecting liquid and flexible enough to sneeze the disinfecting liquid from the bristles of the toothbrush when the toothbrush is drawn through the slit. A reusable lid which can provide a liquid-tight closure is also provided.

14 Claims, 1 Drawing Sheet

(TWO UNIT ALTERNATE)

DISINFECTING TOOTHBRUSH CONTAINER

THE FIELD OF THE INVENTION

The instant invention relates to a toothbrush container and a method for disinfecting a toothbrush and/or storing it under sanitary conditions.

THE BACKGROUND OF THE INVENTION

The toothbrush is used to remove food particles from the cracks between and in our teeth and thus is an invaluable aid in a program of oral hygiene. However a toothbrush which is left sitting on a bathroom sink or other location may collect germs and dirt. These germs and dirt can be introduced into the mouth when the toothbrush is used.

In a recent controlled scientific study of people with oral inflammatory diseases and normal healthy individuals without such oral diseases significantly more potentially harmful bacteria were found on the toothbrushes belonging to those having the oral inflammatory diseases. As a result the ADA(American Dental Association) now recommends changing toothbrushes every four weeks if you are healthy and more often if you are having related health problems.

Furthermore if a toothbrush is allowed to sit in a bathroom fixture in a bathroom which is used by more than one individual, for example in a dormitory, hospital or the like, the toothbrush might inadvertently be used by an individual other than the owner. It is also conceivable that the individual who inadvertently used the toothbrush which is not his or hers has a communicable disease and that active germs reside in his or her mouth. This disease could range from the common cold to AIDS/(acquired immune deficiency syndrome).

While toothbrushes are sold in plastic cases and closed containers exist in which a careful person could store a toothbrush in the bathroom, it would still be susceptible to contamination to some degree and inadvertent use by one who is not the owner of the toothbrush.

It is an object of our invention to provide an improved container for one or more toothbrushes which prevents germs in the air and dirt from collecting on the toothbrushes.

It is another object of our invention to provide a toothbrush container for one or more toothbrushes which automatically disinfect toothbrushes which are properly inserted in it.

It is a further object of our invention to provide an attractive appealing toothbrush container for a toothbrush which prevents communication of disease-causing germs by deliberate or inadvertent use of the toothbrush by individuals who are not the owners of the toothbrush.

It is an additional object of our invention to help prevent the spread of AIDS by an oral pathway by providing a disinfecting toothbrush container which is particularly useful in hospital or dormitory-like surrounding where more than one individual might use the same toothbrush either accidently or deliberately.

SUMMARY OF THE INVENTION

According to our invention a disinfecting toothbrush container for holding a toothbrush and disinfecting the bristles of the toothbrush comprises a container body having a plurality of container chambers formed by dividing the container body by a plurality of substantially vertical container chamber walls. Advantageously two to four container chambers are provided. The container chambers and the container body are divided transversely by a substantially transverse flexible partition having a slit in each of the container chambers large enough for insertion of the toothbrush. The transverse flexible partition divides the container chambers into an upper portion containing air and a lower portion containing a disinfecting liquid. The lips of the slits are firm enough to prevent dirt and germs from the air from entering the disinfecting liquid. Then the toothbrush can be inserted in the disinfecting liquid through the slit in the flexible partition and left so that the disinfecting liquid kills the germs on the bristles. However the slits in the rubber partition are also flexible enough to squeeze the disinfecting liquid from the bristles of the toothbrush when the toothbrush is again withdrawn from the slit. A reusable lid can provide a liquid-tight closure of the container body which is useful for retaining disinfecting liquid.

The flexible partition may be made of rubber. Furthermore the upper portion of the container body is advantageously circular cylindrical while the lower portion may be flared outwardly uniformly and the container may be provided with a substantially flat base so that the container body is comparatively stable when sitting on a flat surface.

The instant invention also provides a method for disinfecting a toothbrush comprising enclosing a disinfecting liquid at least partially by a rubber or flexible partition having a slit wide enough to accept a toothbrush, inserting the end of the toothbrush having the bristles on it into the disinfecting liquid by passing it through the slit in the partition and, after sufficient time to kill the germs on the bristles, withdrawing the toothbrush from the disinfecting liquid and possibly rinsing it.

The disinfecting toothbrush container according to our invention provides a means of preventing transfer of germs and diseases between individuals who might deliberately or inadvertently use the same toothbrush. This could be used to help prevent the, transfer of communicable diseases such as AIDS in institutional circumstances, particularly a dormitory or hospital.

BRIEF DESCRIPTION OF THE DRAWING FIGURES

DETAILED DESCRIPTION OF THE INVENTION

Figure 1:
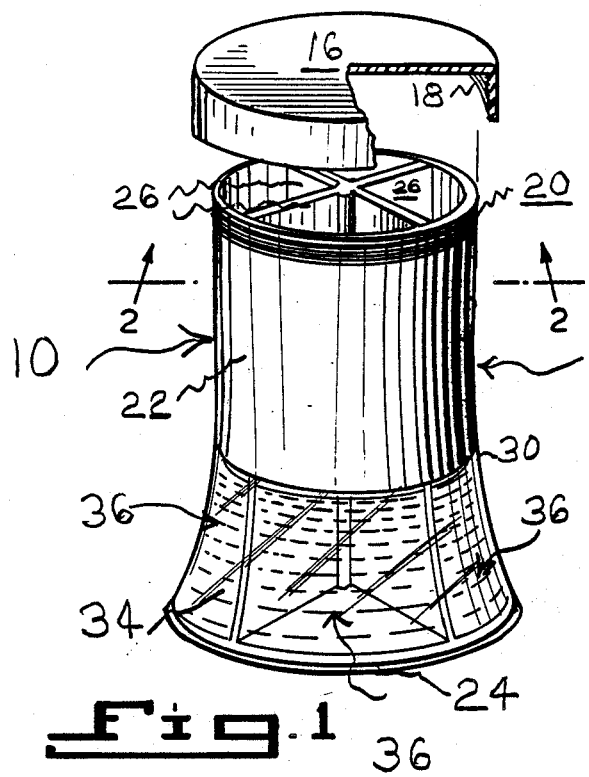
FIG. 1 is a perspective view of an embodiment of the disinfecting toothbrush container according to the instant invention with its lid removed.
Figure 3:
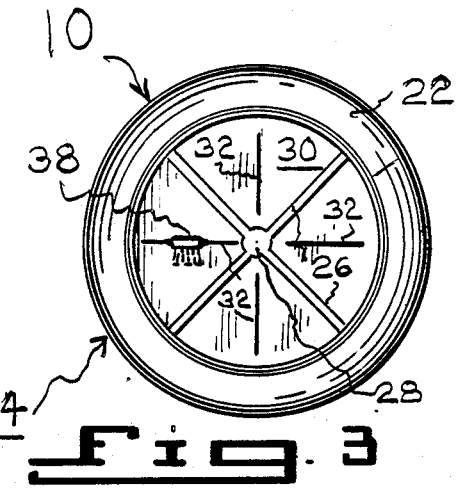
FIG. 3 is a top plan view of the toothbrush container of FIG. 1 with the lid removed.
Figure 4:
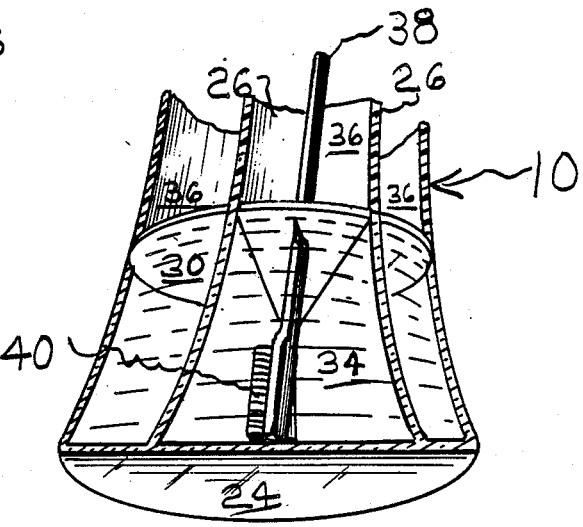
FIG. 4 is a cutaway perspective view of the disinfecting toothbrush container according to FIG. 1 with a toothbrush inserted.
Figure 2:
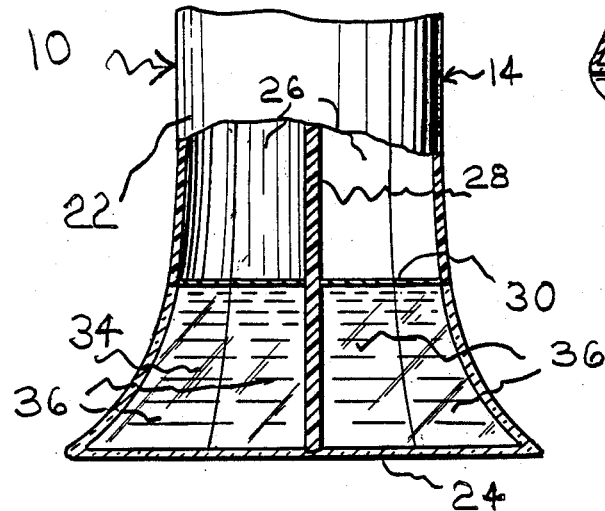
FIG. 2 is an axial cross sectional view through the toothbrush container shown in FIG. 1 taken along the section line 2—2.

FIGS. 1 to 4 show one embodiment of the disinfecting toothbrush container 10 which has four container chambers 36 for holding toothbrushes 38.

This disinfecting toothbrush container 10 comprises a container body 14 with an outer wall 22 divided by four substantially vertical partitioning walls 26 into four substantially equal toothbrush container chambers 36 and a lid 16. The partitioning walls 26 meet at a common center post 28 to which they are attached.

The lid 16 is provided with a plurality of interior threads 18 by which it can be screwed on the upper end of the container body 14 on exterior threads 20 provided on the outer upper edge of the container body 14. When this lid 16 is secured on the container body 14 it provides a liquid-tight closure of the container 10.

While the container body 14 is round and nearly circular cylindrical in its top portion, its bottom portion is flared out uniformly circumferentially and the container body 14 is provided with a flat base 24 so that inadvertent tipping over of the toothbrush container 10 is minimized.

The container chambers 36 and the toothbrush container 10 as a whole are divided into top and bottom portions by the transverse partition 30. The transverse partition 30 is made of a flexible material. In this embodiment the material from which the transverse partition 30 is made is rubber. A substantially radially-extending slit 32 is provided in each of the four portions of the transverse partition 30 corresponding to and in each of the container chambers 36. It is large enough so that a toothbrush 38 can pass through it. A disinfecting liquid 34 is provided below the transverse partition 30 completely filling the lower portions of the container chambers 36.

This disinfecting liquid 34 can be any of a number of germ-killing liquids including Listerine, Cephacol or the like which may contain substances such as alcohol, cetylpyridinium chloride and so forth.

The lips of the slits 32 seal tight enough so that the disinfecting liquid 34 does not substantially evaporate or is not spilled if the container 10 is tipped over and dirt and air are kept out of the lower portions of the container chambers 36. When the toothbrush container 22 sits upright the lid 16 can be removed and a toothbrush 38 can be thrust with the end having the bristles 40 directed downward into the disinfecting liquid 34. The lid 16 can be screwed on the container body 14 again and the toothbrush 38 stored in the toothbrush container 10. While the toothbrush 38 is stored with the bristles 40 in the disinfecting liquid 34 the disinfecting liquid 34 acts to kill the germs present on the toothbrush 38. Naturally when the toothbrush 38 is removed from the container 10 the bristles 40 can be rinsed to remove inert matter. Furthermore the lips of the slit 32 squeeze off disinfecting liquid 34 remaining on the bristles 40 as the toothbrush 38 is drawn through the slit 32.

Figure 5:
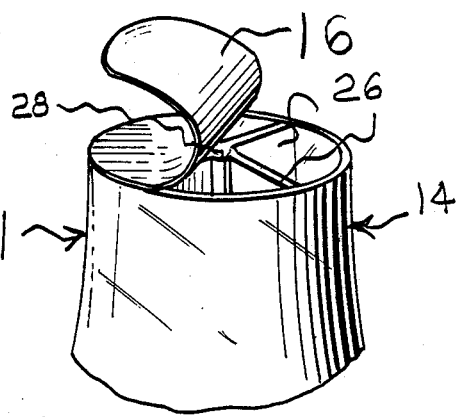
FIG. 5 is a perspective view of the top portion of another embodiment of the toothbrush container according to the instant invention with an alternative type of lid.

Alternatively in another embodiment of the toothbrush container 11 shown in FIG. 5 for easy rapid use the lid 162 can be a substantially flat aluminum piece which is shaped to fit the top of the container body 22. This piece can be applied with a soft seal to the upper edge of the container body 22 and also can be easily and quickly removed.

Figure 6:
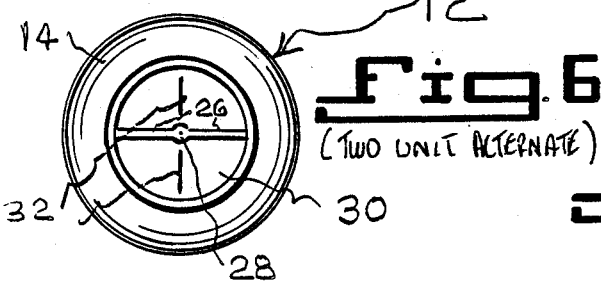
FIG. 6 is a top plan view of an additional embodiment of the toothbrush container according to the instant invention.

In an additional embodiment of the toothbrush container 12 shown in cross section in FIG. 6 only two container chambers 36 are included. It would clearly be adantageous not to put too many toothbrushes in these toothbrush containers 10-12 since disinfecting liquid 34 is gradually reduced in potency with use. Advantageously one toothbrush should be stored in each container chamber 36.

LIST OF REFERENCE NUMBERS 10 first embodiment of the toothbrush container
11 second embodiment of the toothbrush container
12 additional embodiment of the toothbrush container
14 container body
16 container lid
18 interior threads on lid
20 exterior threads on container body
22 outer wall
24 container base
26 vertical container chamber walls
28 center post
30 transverse partition (rubber)
32 radially-extending slits
34 disinfecting liquid
36 container chamber
38 toothbrush
40 bristles It will be understood that each of the elements described above, or two or more together, may also find a useful application in other devices differing from the type of device described above.

The invention is not intended to be limited to the details provided above and it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed is new and what is desired to be protected by Letters Patent is set forth in the following claims:

1. A disinfecting toothbrush container comprising:
    a container body having a substantially flat base and side wall flared circumferentially outward toward said base so that the container is prevented from tipping over; and
    a flexible transverse partition in said container body, said flexible transverse partition cooperating with said base and said side wall to form a disinfecting chamber in a first interior portion of said container body, said transverse partition being flexible enough to allow insertion of a toothbrush therethrough into said chamber and to reseal said chamber when the toothbrush is removed so that said chamber is substantially liquid-tight and dirt from the air is prevented from entering said chamber.

2. The disinfecting toothbrush container of claim 1 further comprising:
    at least one vertical internal wall in said chamber body, said internal wall providing multiple chambers so that multiple toothbrushes can be inserted into respective chambers.

3. A disinfecting toothbrush container according to claim 2 wherein said container body flares uniformly outward from an upper portion of said container body that is circular cylindrical and said vertical internal walls meet in a common center post in said container body.

4. The disinfecting toothbrush container of claim 1 wherein said chamber is completely filled with a disinfecting liquid and said flexible transverse partition includes a slit adapted to permit the insertion and removal of the toothbrush, said slit having lips that seal tightly enough to prevent spillage of said liquid from said chamber.

5. The disinfecting container of claim 4 wherein said flexible transverse partition is firm enough to squeeze disinfecting liquid from bristles of a toothbrush when the toothbrush is withdrawn through said slit from one of said chambers.

6. The disinfecting container of claim 1 wherein said transverse partition is substantially parallel to said base.

7. The disinfecting container of claim 1 wherein of the side wall is substantially perpendicular to said base above said first interior portion.

8. A disinfecting toothbrush container according to claim 1 wherein said transverse flexible partition is made of rubber.

9. A disinfecting toothbrush container comprising:
  a container body having a substantially flat base and side wall flared circumferentially outward toward said base so that the container is prevented from tipping over;
  a flexible transverse partition in said container body, said flexible transverse partition cooperating with said base and said side wall to form a chamber in a first interior portion of said container body, said transverse partition being flexible enough to allow insertion of a toothbrush therethrough into said chamber and to reseal said chamber when the toothbrush is removed so that said chamber is substantially liquid-tight and dirt from the air is prevented from entering said chamber;
  a second internal portion above said transverse partition, said second internal portion being adapted to accommodate the toothbrush handle; and
  a removable lid adapted to close said container body so as to render said container substantially liquid tight.

10. The disinfecting toothbrush container of claim 9 wherein said lid is a flat aluminum piece affixed to an upper edge of said side wall by a soft seal so that said lid can be easily and quickly removed.

11. A disinfecting toothbrush container according to claim 9 wherein the upper edge of said container body is provided with exterior threads and said lid is provided with interior threads so that said lid may be screwed onto said container body.

12. A method of disinfecting a toothbrush having a plurality of bristles at one end, said method comprising the steps of:
  (a) filling a chamber with a disinfecting fluid, said chamber being formed by a flexible transverse partition inside a container body, said container body having a substantially flat base and a side wall flared circumferentially outward toward said base so that the container is prevented from tipping over, said partition being flexible enough to allow insertion of a toothbrush therethrough into said chamber and to reseal said chamber when the toothbrush is removed so that said chamber is substantially liquid-tight and dirt from the air is prevented from entering said chamber;
  (b) inserting the end of said toothbrush having said bristles through said partition into said disinfecting fluid and leaving said bristles in said disinfecting fluid for a time long enough for said disinfecting liquid to act to kill germs on said bristles; and
  (c) withdrawing said toothbrush from said disinfecting fluid through said partition so that disinfecting fluid remaining on said bristles is removed by said partition.

13. The method of claim 12 wherein multiple toothbrushes are inserted through respective slits in the partition.

14. The method of claim 12 further comprising the steps of closing said container body with a removable lid so as to enclose the toothbrush handle in the container and to render said container substantially liquid tight.

* * * * *